US006485298B2

(12) United States Patent
Chishti et al.

(10) Patent No.: US 6,485,298 B2
(45) Date of Patent: *Nov. 26, 2002

(54) SYSTEM AND METHOD FOR RELEASING TOOTH POSITIONING APPLIANCES

(75) Inventors: Muhammad Chishti, Sunnyvale, CA (US); Loc X. Phan, Milpitas, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/099,187

(22) Filed: Mar. 13, 2002

(65) Prior Publication Data

US 2002/0142258 A1 Oct. 3, 2002

Related U.S. Application Data

(63) Continuation of application No. 09/757,385, filed on Jan. 8, 2001, which is a continuation of application No. 09/250,962, filed on Feb. 16, 1999.
(60) Provisional application No. 60/110,189, filed on Nov. 30, 1998.

(51) Int. Cl.[7] ................................................. A61D 5/00

(52) U.S. Cl. ........................................................ 433/6

(58) Field of Search .............................. 433/6, 18, 24, 433/80, 215

(56) References Cited

U.S. PATENT DOCUMENTS

| 3,407,500 | A | 10/1968 | Kesling |
| 3,950,851 | A | 4/1976 | Bergersen |
| 4,526,540 | A | 7/1985 | Dellinger |
| 4,591,341 | A | 5/1986 | Andrews |
| 4,755,139 | A | 7/1988 | Abbatte et al. |

(List continued on next page.)

FOREIGN PATENT DOCUMENTS

WO    WO 98/58596    7/1998

OTHER PUBLICATIONS

Chiappone, "Constructing the gnathologic setup and positioner" *J. Clin. Orthod.* (1980) 14:121–133.
Cottingham, "Gnathologic clear plastic positioner" *Am. J. Orthod.* (1969) 55:23–31.
Cureton, "Correcting malaligned mandibular incisors with removable retainers" *J. Clin. Orthod.* (1996) 30:390–395.
Kesling, "Coordinating the predetermined pattern and tooth positioner with conventional treatment" *Am. J. Orthod. Oral. Surg.* (1946) 32:285–293.
Kesling, "The philosophy of t'1 qhe tooth positioning appliance" *Am. J. Orthod. Oral. Surg.* (1945) 31(6):297–304.
Kleemann et al., "The speed positioner" *J. Clin. Orthod.* (1996) 30:673–680.
Product Brochure, Tru–Tain Orthodontic & Dental Supplies, Rochester, Minnesota 55902, 16 pages total.
*Raintree Essix*™ & *ARS Materials, Inc.*, Raintree Essix™ Technical Magazine Table of Contents and Essix™ Applications, http:/www.essix.com/magazine/default.html (Aug. 13, 1997) 7 pages total.

(List continued on next page.)

Primary Examiner—Todd E. Manahan
(74) Attorney, Agent, or Firm—Townsend and Townsend and Crew LLP; Bao Tran

(57) ABSTRACT

An improved dental appliance system, and methods for using and fabricating the improved appliance, including a polymeric overlay or shell having a teeth-receiving cavity formed therein. The dental appliance having the necessary stiffness or strength to firmly secure the appliance on the teeth and provide controlled forces required for repositioning the teeth, until such time as removal of the appliance is desired. The appliance may be configured for use with a removal mechanism. The removal mechanism provides for selective release of the appliance from the teeth as the removal mechanism undergoes a state change stimulated by an environmental stimulus or environmental switch.

36 Claims, 5 Drawing Sheets

U.S. PATENT DOCUMENTS

| | | | |
|---|---|---|---|
| 4,793,803 A | * 12/1988 | Martz | 433/6 |
| 4,798,534 A | 1/1989 | Breads | |
| 4,856,991 A | 8/1989 | Breads et al. | |
| 4,983,334 A | * 1/1991 | Adell | 433/6 |
| 5,035,613 A | 7/1991 | Breads et al. | |
| 5,055,039 A | 10/1991 | Abatte et al. | |
| 5,059,118 A | * 10/1991 | Breads et al. | 433/6 |
| 5,186,623 A | 2/1993 | Breads et al. | |
| 5,645,421 A | 7/1997 | Slootsky | |

OTHER PUBLICATIONS

Shilliday, "Minimizing finishing problems with the mini–positioner" *Am. J. Orthod.* (1971) 59:596–599.

Warunek et al., "Clinical use of silicone elastomer appliances" *JCO* (1989) XXIII(10):694–700.

Wells, "Application of the positioner appliance in orthodontic treatment" *Am. J. Orthodont.* (1970) 58:351–366.

* cited by examiner

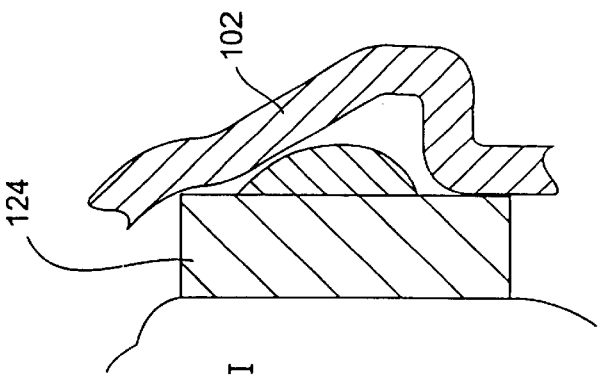
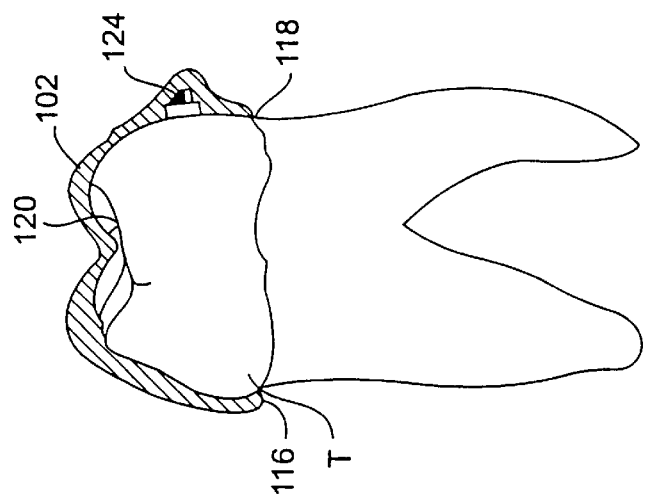
FIG. 3
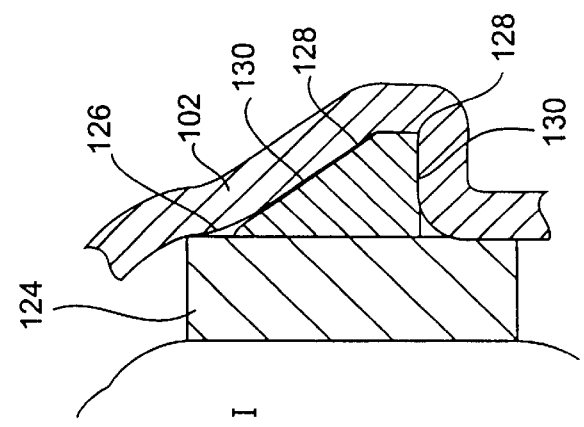

SYSTEM AND METHOD FOR RELEASING TOOTH POSITIONING APPLIANCES

CROSS-REFERENCES TO RELATED APPLICATIONS

The present application is a continuation of Application No. 09/757,385 filed Jan. 8, 2001, which was a continuation of U.S. application No. 09/250,962, filed Feb. 16, 1999, which claimed the benefit and priority of U.S. Provisional Patent Application No. 60/110,189 filed Nov. 30, 1998. The full disclosures of which are hereby incorporated by reference for all purposes.

BACKGROUND OF THE INVENTION

1. Field of the Invention

The present invention is related generally to the field of orthodontics. More particularly, the present invention is related to improved dental appliances and systems, and methods for using and making the same.

Elastic positioners optionally in combination with attachments to the patient's teeth are employed in orthodontic treatments for controlled tooth movement to a predetermined position. In providing such appliances and treatments, it is important to move teeth to an ideal predetermined position with gentle controlled forces. Typically, the appliance is fabricated to provide accuracy of placement in compliance with the exact shape of the teeth or the exact shape and placement of the attachment device.

The use of elastic positioners for repositioning teeth is known. Such elastic positioners comprise a thin shell of elastic material that generally conforms to a patient's teeth but is slightly out of alignment with the initial tooth configuration. By properly choosing the configuration, placement of the elastic positioner over the teeth will move individual teeth to desired intermediate or final positions over time. Of particular interest to the present invention, a system comprising multiple elastic tooth positioning appliances for performing orthodontic procedures is described in published PCT application WO98/58596 which corresponds to co-pending application serial number 08/947,080, assigned to the assignee of the present application.

The resilient repositioning forces required to move a tooth from one position to another position in a reasonable amount of time may be formidable. The design of appliances capable of imparting such forces with acceptable comfort and appearance has been a challenge. To achieve such forces, the appliance must be relatively stiff (i.e. possess a high strength or high modulus) to provide a sufficient grip on the teeth. The stiffness both ensures that the dental appliance remains firmly in position on the patient's teeth and provides the repositioning force necessary to move the teeth. The stiffness also permits the dental appliance to "grab hold" of an anchor device or other surface feature which may be present on the tooth to apply a directed force to execute orthodontic tooth movements.

While appliance stiffness is desirable for providing repositioning forces and for maintaining appliance position on the teeth, the removal of stiff appliances can be difficult. Tooth positioners which are stiff and tightly conform to the teeth can require the use of orthodontic tools for removal, making removal by the patient very difficult. Periodic removal is desirable for a number of purposes including cleaning, dental hygiene, removal before meals, removal for cosmetic purposes, and removal and replacement in the course of treatment. In most or all of these cases, however, it will be inconvenient for the patient to visit the practitioner. Moreover, the use of tools can damage the appliance, making its reuse difficult or impossible.

For these reasons, it would be desirable to provide alternative methods, appliance designs, and systems for removing a dental appliance from the teeth. Such methods and apparatus, systems should be economical and, in particular, should reduce the difficulty experienced and the amount of time required by the practitioner and/or patient in removing and subsequently re-applying the appliance. At least some of these objectives will be met by the methods and systems of the present invention described hereinafter.

2. Description of the Background Art.

WO98/5896 and co-pending application Ser. no. 08/947,080 are referenced above. Tooth positioners for finishing orthodontic treatment are described by Kesling in the Am. J. Orthod. Oral. Surg. 31:297–304 (1945) and 32:285–293 (1946). The use of silicone positioners for the comprehensive orthodontic realignment of a patient's teeth is described in Warunek et al. (1989) J. Clin. Orthod. 23:694–700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139.

Other publications describing the fabrication and use of dental positioners include Kleemann and Janssen (1996) J. Clin. Orthodon. 30:673–680; Cureton (1996) J. Clin. Orthodon. 30:390–395; Chiappone (1980) J. Clin. Orthodon. 14:121–133; Shilliday (1971) Am. J. Orthodontics 59:596–599; Wells (1970) Am. J. Orthodontics 58:351–366; and Cottingham (1969) Am. J. Orthodontics 55:23–31.

BRIEF SUMMARY OF THE INVENTION

The present invention provides improved dental appliances and methods for using and fabricating such appliances. Individual appliances comprise a polymeric shell having a teeth-receiving cavity formed therein. The shell will have the necessary stiffness to firmly secure the appliance on the teeth and provide controlled forces required for repositioning the teeth. As discussed in detail below, one or more removal features or mechanisms will be provided to facilitate removal of the appliances from the teeth. The removal mechanism may be an integral property or characteristic of the shell and/or may be a separate component or components in addition to the shell. Exemplary shell properties include changes in stiffness or shape induced by exposure of the shell to different environmental conditions, e.g. a change in temperature, a change in pH, a change in ionic strength, or the like. Exemplary additional components include adhesives, interface layers (between the shell and the tooth), tooth anchors, reinforcement components (layers, filaments, braids, etc.), where such components can change stiffness, dimensions, orientations, or the like to selectively hold or release the shell onto the teeth. Usually, the changes in the additional components will be induced by the same types of environmental changes used for inducing property changes in the shell. Alternatively, removal mechanisms comprising separate components could be stimulated by exposure to an external energy source, e.g. being mechanically, electrically, optically, magnetically or otherwise triggered to induce a change which causes or permits release of the shell from the teeth.

Use of such removal mechanisms is advantageous in a number of respects. Environmental changes can be easily implanted by a practitioner or patient. For example, the practitioner or patient can wash the mouth with an appropriately heated, pH-modified, ionic strength controlled, or other solution which can induce the desired change in the removal mechanism. While the use of mechanically, electrically, or optically triggered removal mechanisms may require additional equipment, such mechanisms can also be very simple and suitable for use by the patient as well as the practitioner. In all cases, the removal mechanisms can usually be made reversible, i.e. the appliance can be "switchable" between attached configurations where the appliance will remain in place on the teeth and a release configuration where the appliance can be removed form the teeth. This is a particular advantage since is allows the appliance to be temporarily "reconfigured" and removed for any purpose and then repositioned over the teeth to continue the treatment.

In a first aspect of the invention, a state change reduces the stiffness or shape (or both) of the shell material such that the engagement forces between the shell and the teeth or other interfaces are reduced or eliminated. The state change can be a change in any material property which affects stiffness or shape, such as hardness/softness (as measured by durometer), elasticity, phase (as with shape memory polymers and materials), or the like. Preferably, the state change will be reversible so that the shell can recapture the stiffness lost or recover the shape which was lost while undergoing the initial state change. The reduction of stiffness will usually comprise a softening and/or increasing elasticity of the shell material, permitting the shell to become more easily pulled from over the teeth. A change in shape will reduce or eliminate engagement forces between the appliance and the teeth or other interfaces due to an expansion, contraction, partial opening, reduction of interference, or other reconfiguration of the appliance. The desired state change will preferably be induced by an environmental change which can easily be effected in the patient's mouth. Preferred environmental changes are these which can be implemented by a simple mouth wash with a solution having a particular composition, pH, temperature, ionic strength or other property. The selected property should be one that the patient will not normally encounter in daily life, at least during periods when release of the appliance is not intended. For example, temperature would not be a good choice unless it is intended that the appliance be removed when eating or drinking hot foods and drinks. The property should also be one that is physiologically acceptable, e.g. very high or very low pH might not be desirable.

It is not necessary, however, that the "released" configuration be long term or sustainable. In many instances, the removal mechanism will permit mounting of the appliance onto the teeth when the removal mechanism is in its "attached" configuration. To remove the appliance, the released configuration need be sustained only long enough to complete the removal. The removal mechanism can then revert to the attached configuration, as the result of for example, cooling, pH change, and ionic strength change, and still be replaced over the teeth without the need to restore the released configuration.

In one embodiment, the removal mechanism may be an integral property of the appliance, usually being an inherent property of the shell or a part of the shell. An orthodontic appliance is provided which has a shell formed of at least one layer of a polymeric material. The shell has a cavity which fits closely over a contiguous group of teeth. A contiguous group of teeth includes at least 3 teeth, but usually 4 or more. The at least one layer of polymeric material has a first state where the appliance is held onto the teeth and a second state where the appliance may be removed from the teeth. The first state will exist when the shell is in place in the patient's mouth in the absence of any "non-oral" conditions or externally applied energy or other stimuli. The second state can then be selectively induced by creating a "non-oral" environment in the patient's mouth, as discussed above. The non-oral environment may consist of a non-physiological temperature (above 37° C., preferably 40–55° C.; or below 37° C., preferably below 30° C.), a non-physiologic pH (above 8, preferably above 9, more preferably above 8.5 or below 7, preferably below 6, more preferably below 6.5), a non-physiologic ionic strength, such as 3% sodium chloride, or the like.

In another embodiment, the removal mechanism is formed as one or more additional component(s) or mechanism(s). Such systems will include at least one polymeric shell which can be removably placed over a patient's teeth. The separate removal component or mechanism is switchable from a first state to a second state.

In yet another embodiment, a dental appliance system will include a dental appliance, which has a shell with a cavity. The system will further include an attachment device which is formed or exists separately from the shell. The attachment device is usually configured to be positioned between the outer surface of the teeth and an inner surface of the cavity. The device is switchable between a first state, where the appliance is held onto the teeth, and a second state, where the appliance may be removed from the teeth. The switch is stimulated or made to occur as a response to an environmental change.

In another aspect of the invention, an improved method is provided for removing an appliance from the teeth. Preferably, the appliance is a polymeric shell, which has cavities shaped to receive and resiliently reposition teeth to produce a final tooth arrangement. In a first aspect, the improvement comprises transforming the shell from a first state, where the appliance is held onto the teeth, to a second state where the appliance may be removed from the teeth. The transformation is performed in situ in the patient's mouth, usually the exposure to an environmental change or external stimulus as described above. The transformation is repeatable so that the appliance can be reinserted.

In another aspect a method for fabricating a removable incremental tooth position adjustment appliance is provided including forming a shell of at least one layer of a polymeric material with a teeth mold. The shell is formed with cavities shaped to receive and resiliently reposition teeth from one arrangement to a successive arrangement. The shell transforms from a first state, where the appliance is held onto the teeth, to a second state, where the appliance may be released from the teeth.

In another aspect, an appliance system comprises a plurality of individual appliances that can be used for repositioning teeth from an initial tooth arrangement to a final tooth arrangement using a plurality of dental incremental position adjustment appliances. In this embodiment, the plurality of position adjustment appliances will include a first appliance having a geometry selected to reposition the teeth from the initial tooth arrangement to a first intermediate arrangement. The plurality of position adjustment appliances will also have one or more intermediate appliances having geometries selected to progressively reposition the teeth from the first intermediate arrangement to successive intermediate arrangements. The position adjustment appliances will still further have a final appliance having a geometry selected to progressively reposition the teeth from the last intermediate arrangement to the final tooth arrangement. The system will also include a removal mechanism formed into each adjustment appliance described above. The removal mechanism transforms from a first state to a second state to release each appliance from the teeth. In a preferred embodiment, the transformation is activated by a stimulus, preferably an environmental stimulus or condition.

BRIEF DESCRIPTION OF THE DRAWINGS

FIGS. 3, 3A, and 3B are cross-sectional views of an attachment device for securing the appliance of FIG. 1 on to the teeth.

DETAILED DESCRIPTION OF THE INVENTION

Figure 1:
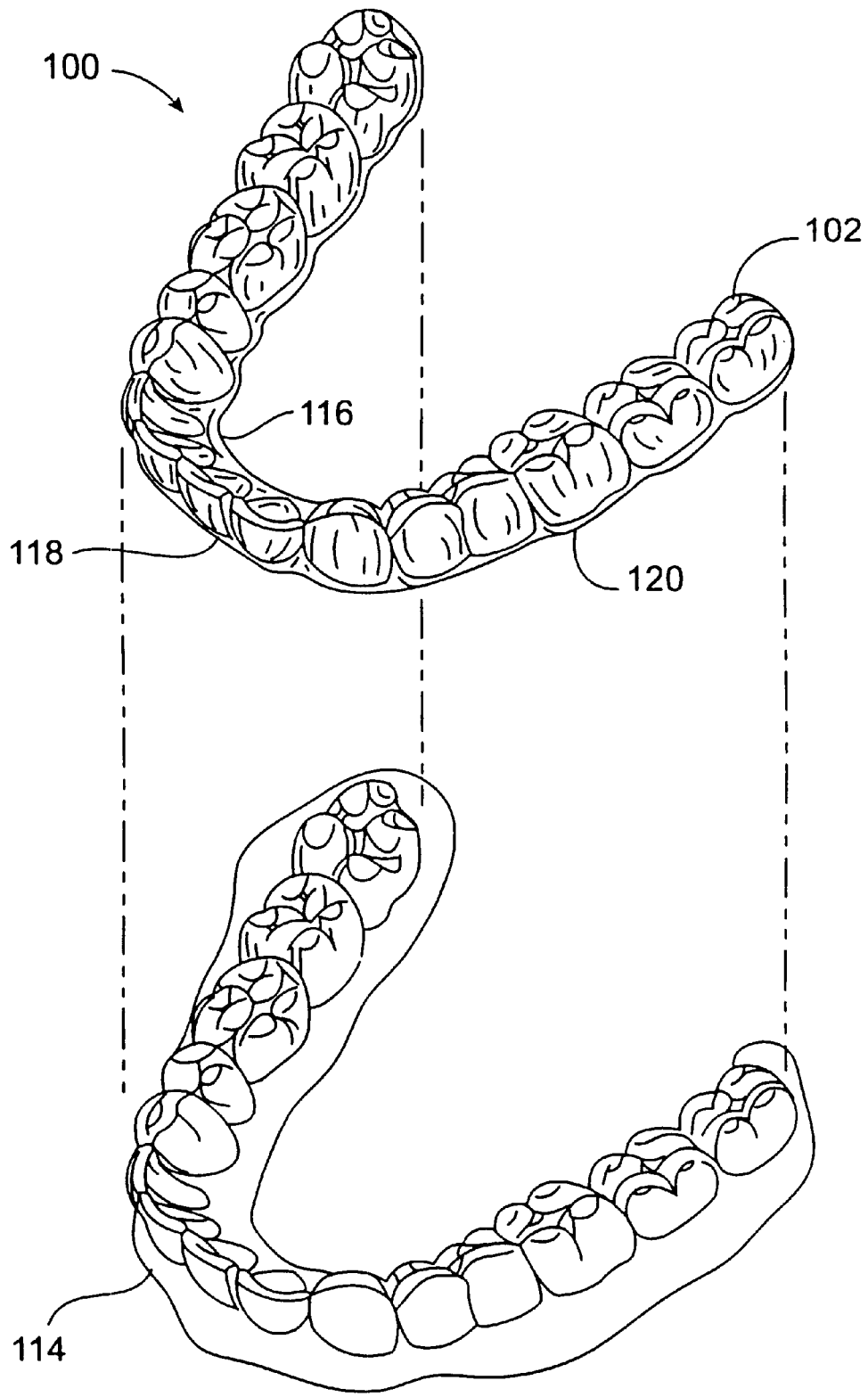
FIG. 1 illustrates the jaw of a patient together with a dental appliance which has been configured according to the present invention.

Referring to FIG. 1, the apparatus, systems, and methods according to the present invention will include at least one appliance 100 removably replaceable over the teeth. Usually, appliance 100 is one of a plurality of incremental position adjustment appliances. The appliances are intended to effect incremental repositioning of individual teeth in the jaw. The appliance 100 may be used in place of any of the known positioners, retainers, or other removable appliances which are known for finishing and maintaining teeth positions in connection with orthodontic treatment. The appliances of the present invention, in contrast with prior apparatus and systems, are particularly suitable for use by a patient successively in order to achieve gradual tooth repositioning. A full description of an exemplary repositioning appliance is described in co-pending U.S. application Ser. No. 08/947,080 filed Oct. 10, 1997, which is herein incorporated by reference for all purposes. A description of this exemplary dental appliance for use with the removal mechanism of the present invention is described below.

The exemplary appliance 100 includes a polymeric shell 102 having an inner cavity 120, a proximal edge 116, and a distal edge 118. Cavity 120 is shaped to receive and resiliently reposition teeth from one tooth arrangement to a successive tooth arrangement. The polymeric shell will preferably, but not necessarily, fit over all teeth present in the upper or lower jaw 114. Often, only certain one(s) of the teeth will be repositioned while others of the teeth will provide a base or anchor region for holding the repositioning appliance in place as it applies the resilient repositioning force against the tooth or teeth to be repositioned. The gums and/or the palette can also serve as an anchor region, thus allowing all or nearly all of the teeth to be repositioned simultaneously. Additionally, anchors and adhesives, which are described in more detail below, are available which may also serve as attachment points for appliance 100. What follows is a description of various embodiments for securing appliance 100 to the teeth.

Figure 2B:
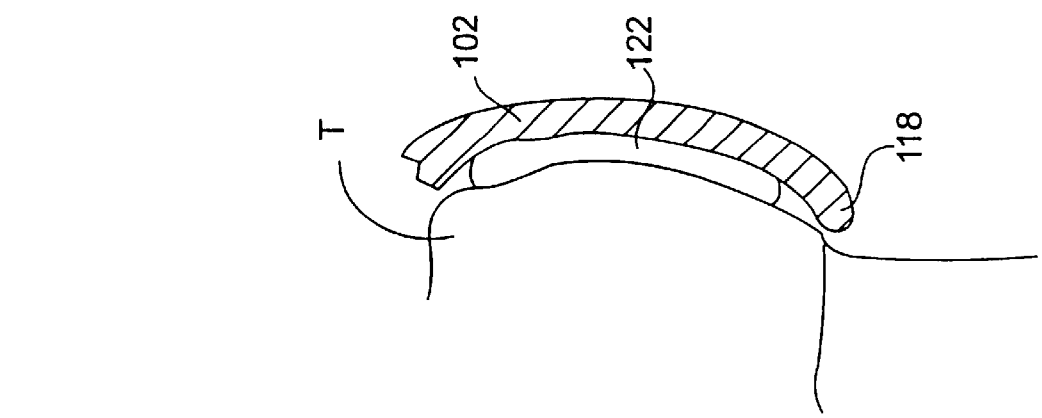
FIGS. 2, 2A, and 2B are cross-sectional views of embodiment for securing the appliance of FIG. 1 on to the teeth.
Figure 2:
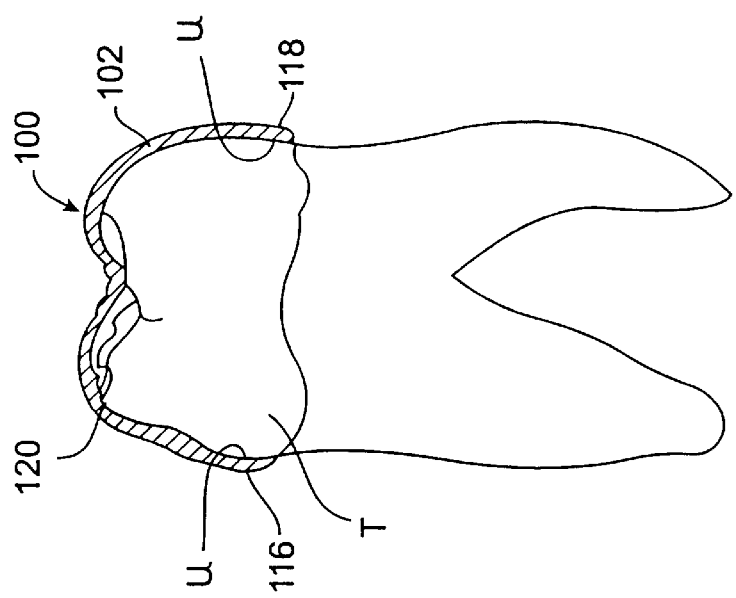
Figure 2A:
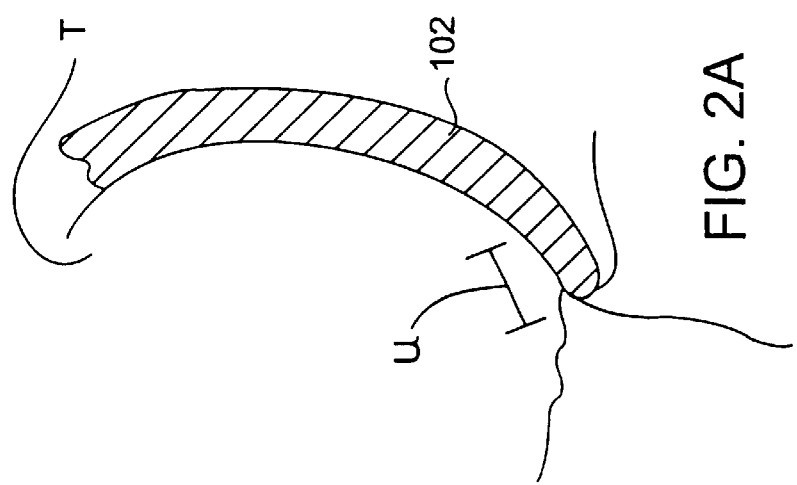

As can be best understood with reference to FIGS. 2, 2A, and 2B, shell 102 is forced down over teeth T, typically by the patient biting down on the shell or by other forms of manual pressure being applied to the shell. Edges 116 and 118 are made to engage what is known as the undercut U of the teeth. Typically, this type of engagement is helpful in that it allows for specific tooth movements, such as extrusions (i.e. upward movement of the tooth).

Shell 102 is made of a material that has a predetermined modulus, also referred to as the stiffness, of the material. Generally, the modulus is a measurement of the inherent stiffness of a material determined by conducting stress and strain tests on a material specimen and plotting the results. The value of the slope of the line generated by the results is the modulus. The modulus can be predetermined to match the compliance required to reposition the teeth based on requirements set by an individual patient's repositioning needs. In one example, the shell may have a modulus in the range of between about 0.1 GPa to 4 GPa, usually 0.5 GPa to 3 GPa, preferably about 0.8 GPa to 1.5 GPa.

Often, the shell is formed from a material that has uniform properties, particularly stiffness, over the entire area. In some cases, however, it will be desirable to vary the stiffness, thickness, or other material properties of the shell at different points or segments. Also, other layers, reinforcement elements, holes, or components may be added to the shell to vary its stiffness and/or other mechanical properties.

The stiffness of the shell keeps edges 116 and 118 engaged with undercut U, which is designed to hold the appliance in place and effect tooth repositioning. The stiffness, however, prevents the shell from being easily removed from the undercut. Therefore, to reduce the effort of removing the shell from the teeth, the shell stiffness can be modified. For instance, in the example above, to reduce the 1 to 4 GPa stiffness between shell 102 and interfaces with the teeth, the stiffness of the shell may need to be temporarily reduced by at least 10%, usually at least 50%, typically by approximately 10% to 90%, more typically about 50% to 90%.

Once shell 102 is in position e.g. engaged with the undercut U of the tooth, the shell provides the desired repositioning forces to the teeth. At such time as desired, shell 102 may then be removed from the teeth. In one embodiment directed at removing the shell, shell 102 may be made of a polymeric material which can undergo a change from a first state to a second state. The state may include, for example a change in material property or a change in shape. The changes can be made to occur throughout the shell, but at least in the region of engagement with the undercut. The changes in material property or shape remove or reduce, as appropriate, the stiffness of the shell, which makes removal of the appliance substantially easier. The shell may include a single layer of material or else a plurality of polymeric materials. Each layer may undergo the property change independent of one another or simultaneously. The layer or layers may also be made of a cross-linked polymer capable of undergoing a change in shape. In this embodiment, shell 102 may be deformed, such that edges 116 and 118 of shell 102 can be made to disengage undercut U, which then allows for easy removal of appliance 100.

In an alternative embodiment, in addition to the engagement with the undercut, or in some cases instead of the engagement with the undercut, an adhesive 122 (FIG. 2B) may be used to add holding strength between appliance 100 and the teeth. The adhesive may have a peel strength that may be reduced or eliminated in order to remove the shell. For example, in its initial state the adhesive should have a peel strength of no less than about 250 g/cm, however, to remove the shell, the peel strength is reduced to a value below the 250 g/cm threshold. Adhesives, with compositions that are side chain crystalizable based polymer such as polyethylacrylate-hexadecylacrylate copolymer with XAMA 2, polypentadecylacrylate with cross linker, polyoctadecylacrylate with XAMA 2, and the like, may be used for such purposes. The ability to reduce the peel strength of the adhesive, facilitates removal of the appliance. In a manner described below, the adhesive can be subjected to an environmental change (e.g. temperature) or other appropriate stimulus to reduce the peel strength. Since the peel strength can be recovered after the environmental change or stimulus is changed or removed, only one application of the adhesive to the shell may be necessary, regardless of the number of times the shell is removed from the teeth.

In another alternative embodiment, shell 102 may also be held or anchored to the teeth through an engagement between shell 102 and an attachment device such as anchor 124 (FIGS. 3, 3A and 3B). Attachment device 124 may be anchored to a distal surface (between tooth and cheek) and/or a proximal surface (between tooth and tongue) of the teeth using an adhesive or similar bonding substance. Various attachment device designs are described in more detail below. Tooth anchors used with convention wire. braces are well known and described in the patent and dental literature. For use in the present invention, the anchors may have any of a variety of material properties with the objective being to point a force-transmitting interface between the appliance and the tooth when the appliance is in place. The anchors may be formed from most solid, physiologically acceptable materials, particularly metals, ceramics, and polymers. The materials may be rigid, resilient, or programmable, e.g. shape memory polymers or metal alloys. In some instances, it is also possible that the anchors would be mechanically complex, e.g. articulated, rotatable, or otherwise repositionable to facilitate mounting or removal of the appliance from the teeth.

Attachment device 124 has an engagement surface 130 that corresponds to an indentation feature 128 formed on the inner surface of cavity 120. As shell 102 is forced onto the teeth T, as described above, inner surface 126 of shell cavity 120 slidingly contacts engagement surface 130 until indentation feature 128 matches up to engagement surface 130. At that time, the indentation 128 conforms around the shape of anchor 124 with a snug fit to hold shell 102 in position. As can be appreciated from the geometric shape of anchor 124 shown in FIGS. 3, 3A, and 3B, the engagement between anchor 124 and shell 102 is a "one-way" engagement, which means shell 102 is substantially locked in position.

In this alternative embodiment, anchor 124 may be made of a polymeric material that can be made to undergo a change in material property. In particular, the combination of the strength of anchor 124, in an initial state, and the strength of shell 102, may be enough to hold shell 102 to the teeth, such that shell 102 may not be easily removed. However, as the material property of the anchor changes, the combination of strengths is reduced. When the strength is reduced below the force being applied to remove shell 102, the shell lifts-off from the teeth. Alternatively, anchor 124 maybe made of a cross-linked polymer. In this alternative embodiment, anchor 124 can undergo a change in shape, which changes the geometry of the anchor such that the engagement between the anchor and the shell is weakened or else removed. Although, the entire shape of the anchor may be changed, the shape change may occur at least in the region of engagement between the anchor and the shell. The anchor may be made of a single layer or a plurality of layers each made of a polymer or cross-linked polymer as described in more detail below.

Shell 102 may also be configured with a reinforcement structure, such as a wire, a filament, a mesh, a ring, and/or a braid. The reinforcement structure may also be of undergoing a change in material property or else a change in shape, such that the change facilitates the removal of the appliance from the teeth. For example, appliance 100 may be fabricated with a polymeric external layer and a metal inner wire embedded in at least a portion of the appliance proximate to either the engagement with the undercut or the engagement with the anchor. The metal inner wire can be made of a memory shape metal, such as Nitinol®, Bimetal®, Memotal® or similar alloy. The wire undergoes a change in material property (and/or shape) as it is subjected to a thermal stimulus or other external stimulus. In this example, the wire changes geometry. Since the wire is embedded within the appliance, the appliance also changes shape, which reduces the shells hold on the teeth.

In a preferred embodiment, the changes described above may be provided through use of various polymers which undergo a glass transition at a preselected temperature, preferably a temperature above the average body temperature. What follow is a description of the various material property and shape changes undertaken by a change in glass transition temperature.

The glass transition may occur by using a plastic, such as a polymer, that has a molecular transition incorporated in the same. The polymeric material is biocompatible and is formulated so that the achieved transition can be activated upon subjecting the appliance to thermal stimuli as hereinafter explained. The molecular transitions, which are incorporated in the appliance, are typically in the form of thermotransitions, as for example, a crystalline melting point, above about 37° C., preferably between 40° C. and 55° C., of the polymer side chain, the polymer main chain, or a liquid-crystal (mesophase) transition of the polymer chain. The thermotransitions may also be accessed via a glass transition phenomenon or a local mode molecular transition. Examples 1–12 provide exemplary lists of such materials.

Figure 4D:
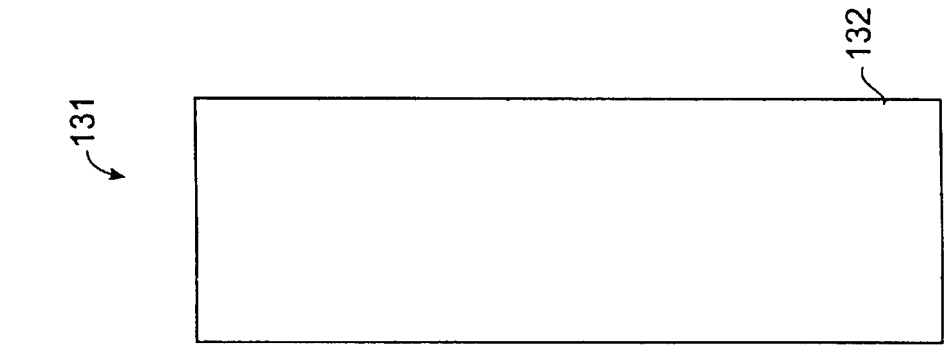
FIGS. 4A–4D are schematic illustrations of the layering geometry used in accordance with the present invention.
Figure 4C:
Figure 4B:
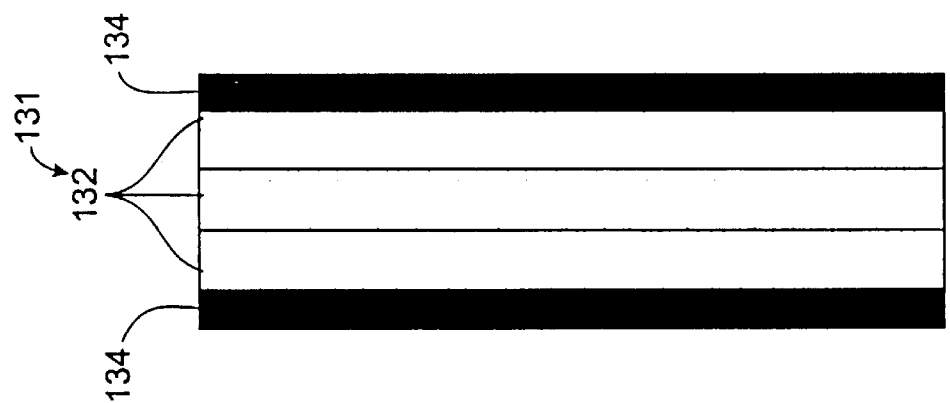
Figure 4A:
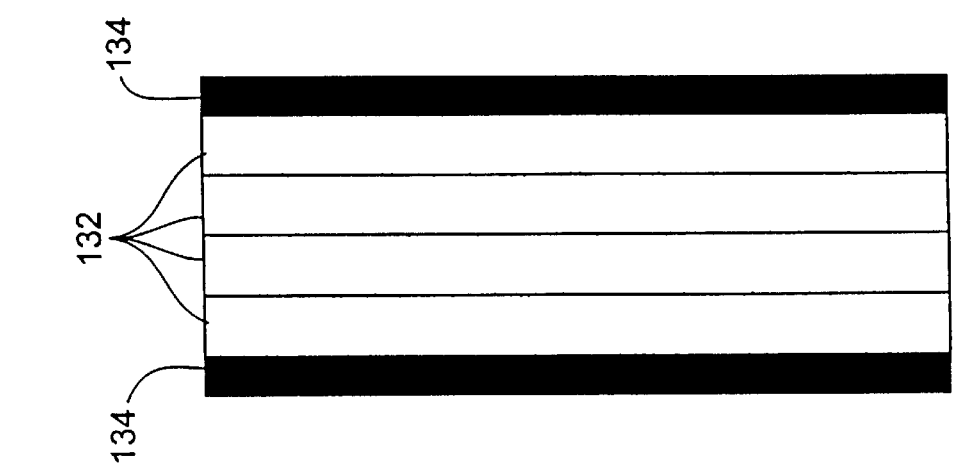

In one embodiment, a glass transition removal mechanism may comprise a single layer or a plurality of material layers 131 configured in shell 102, as shown in FIGS. 4A, 4B and 4C. The shell may include a variable number of layers 132, which may each have variable thickness and/or variable glass transition temperatures. The layers may be formed in various orientations and configurations to suit the modulus and application requirements. The shell layers will be formed by a process, such as thermoforming or similar process, and will have formed on them the desired shell cavities and indentations necessary for proper application of the repositioning forces to the teeth.

| | GLASS TRANSITION POLYMERS | | |
|---|---|---|---|
| Layer | Material | Thickness | Temp. Phase |
| Example 1. | | | |
| 1 | Polycarbonate | 5 mils | Hi Temp. |
| 2 | Polyvinyl chloride (PVC) | 10 mils | Low Temp. |
| 3 | PVC | 10 mils | Low Temp. |
| 4 | PVC | 10 mils | Low Temp. |

GLASS TRANSITION POLYMERS (continued)

| Layer | Material | Thickness | Temp. Phase |
|---|---|---|---|
| 5 | PVC | 10 mils | Low Temp. |
| 6 | Polycarbonate | 5 mils | Hi Temp |
| Example 2. | | | |
| 1 | Polycarbonate | 10 mils | Hi Temp. |
| 2 | PVC | 10 mils | Low Temp. |
| 3 | PVC | 10 mils | Low Temp. |
| 4 | Polycarbonate | 10 mils | Hi Temp. |
| Example 3. | | | |
| 1 | PMMA | 5 mils | Hi Temp. |
| 2 | Polyethelyne (PE) | 10 mils | Low Temp. |
| 3 | PE | 10 mils | Low Temp. |
| 4 | PE | 10 mils | Low Temp. |
| 5 | PE | 10 mils | Low Temp. |
| 6 | PMMA | 5 mils | Hi Temp. |
| Example 4. | | | |
| 1 | PMMA | 10 mils | Hi Temp. |
| 2 | PE | 10 mils | Low Temp. |
| 3 | PE | 10 mils | Low Temp. |
| 4 | PMMA | 10 mils | Hi Temp. |
| Example 5. | | | |
| 1 | Polycarbonate | 5 mils | Hi Temp. |
| 2 | PE | 10 mils | Low Temp. |
| 3 | PE | 10 mils | Low Temp. |
| 4 | PE | 10 mils | Low Temp. |
| 5 | PE | 10 mils | Low Temp. |
| 6 | Polycarbonate | 5 mils | Hi Temp. |
| Example 6. | | | |
| 1 | Polycarbonate | 10 mils | Hi Temp. |
| 2 | PE | 10 mils | Low Temp. |
| 3 | PE | 10 mils | Low Temp. |
| 4 | Polycarbonate | 10 mils | Hi Temp. |
| Example 7. | | | |
| 1 | PMMA | 5 mils | Hi Temp. |
| 2 | PE | 10 mils | Low Temp. |
| 3 | PE | 10 mils | Low Temp. |
| 4 | PE | 10 mils | Low Temp. |
| 5 | PE | 10 mils | Low Temp. |
| 6 | PMMA | 5 mils | Hi Temp. |
| Example 8. | | | |
| 1 | PMMA | 10 mils | Hi Temp. |
| 2 | PE | 10 mils | Low Temp. |
| 3 | PE | 10 mils | Low Temp. |
| 4 | PMMA | 10 mils | Hi Temp. |
| Example 9. | | | |
| 1 | Polycarbonate | 20 mils | Hi Temp. |
| 2 | PE | 20 mils | Low Temp. |
| Example 10. | | | |
| 1 | PMMA | 20 mils | Hi Temp. |
| 2 | PVC | 20 mils | Low Temp. |
| Example 11. | | | |
| 1 | Polycarbonate | 20 mils | Hi Temp. |
| 2 | PVC | 20 mils. | Low Temp. |
| Example 12. | | | |
| 1 | Polysulfone | 20 mils | Hi Temp. |
| 2 | PE | 20 mils | Low Temp. |

In an exemplary embodiment, using the materials as in Example 1 above for illustration purposes, shell 102 may include first, second, and third internal layers 132, each including 10 mils of polyvinyl chloride (PVC) material, having a glass transition temperature of about 50° C. Internal layers 132 are sandwiched between external layers 134, each of 5 mils of Polycarbonate material, which have a glass transition temperature of about 150° C. The Polycarbonate external layers 134 and the PVC inner layers 132, while under the glass transition temperature of both materials should have the combined modulus of all of the layers to provide the shell with the requisite modulus or strength to grab hold of and reposition the teeth. Alternatively, the inner layers may be configured with a higher transition temperature than that of the external layers. By reversing the threshold glass transition temperatures between the layers, the external layers can be made to lose stiffness while the inner layers maintain their stiffness.

In a preferred operation, a thermal stimulus is applied to shell 102. The temperature being above the glass transition temperature of inner layers 132, but below the glass transition temperature of outer layers 134. Once inner layers 132 reach their glass transition temperature, they lose stiffness, thus removing their contribution to the stiffness of shell 102. Since, shell 102 is less stiff, the appliance can be manipulated and removed from the teeth.

External layers 134 provide a structural member or superstructure that is kept from reaching its glass transition temperature so that it maintains its original shape. Thus, once appliance 100 is removed from the teeth, the above process can be reversed. To reverse the process, inner layers 132 may be brought below their glass transition temperature, which will cause inner layers 132 to return to their original high stiffness state. Appliance 100 can then be re-applied to the teeth in the manner described above and will have substantially the same stiffness, and therefore the same effectiveness, as before the initiation of the removal mechanism.

The glass transition removal mechanism may also comprise at least one layer of various different homopolymers, cross-linked homopolymers, and/or copolymer blends of thermoplastics, which have a "built-in" memory capability. The materials, a representative list shown in Examples 13–21 below, are individually selected or blended together to have a preselected glass transition temperature. As shown in FIG. 4D for illustrative purposes, the layer geometry may include a single material layer 132, which may range from about 1.0 mil to 60 mils, preferably 10–40 mils.

GLASS TRANSITION POLYMERS-CROSS-LINKED

| Layer | Material | Thickness | Temp. Phase |
|---|---|---|---|
| Example 13. | | | |
| 1 | Polycapralactone | 40 mils | 40–55° C. |
| Example 14. | | | |
| 1 | Vestenamer | 40 mils | 40–55° C. |
| Example 15. | | | |
| 1 | PMMA/Polyethylene Blend | 40 mils | 40–55° C. |
| Example 16. | | | |
| 1 | Polycarbonate/Polyethylene Blend | 40 mils | 40–55° C. |
| Example 17. | | | |
| 1 | Polysulfone/Polyethylene Blend | 40 mils | 40–55° C. |
| Example 18. | | | |
| 1 | Polyester | 40 mils | 40–55° C. |
| Example 19. | | | |
| 1 | Polyester/Polycarbonate Blend | 40 mils | 40–55° C. |

GLASS TRANSITION POLYMERS-CROSS-LINKED (continued)

| Layer | Material | Thickness | Temp. Phase |
|---|---|---|---|
| Example 20. | | | |
| 1 | Polyurathane | 40 mils | 40–55° C. |
| Example 21. | | | |
| 1 | Polyurathane/Polycarbonate Blend | 40 mils | 40–55° C. |

Figure 5A:
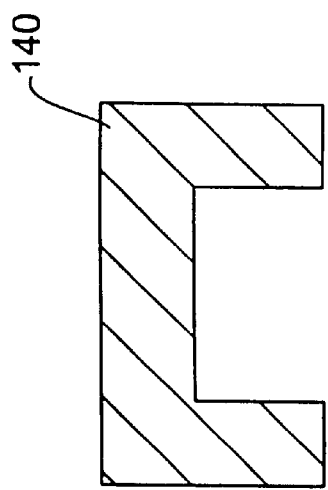
FIGS. 5A–5B are cross-sectional views of a process for forming an appliance in accordance with the present invention.
Figure 5B:
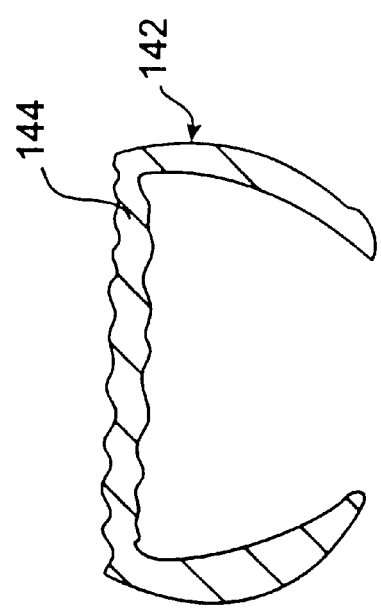

In FIGS. 5A and 5B, the memory removal mechanism, incorporated into shell 102 is shown in various stages of production. To form the memory removal mechanism, materials, such as those provided in Examples 13–21, may be extruded in sheets and then formed into any shape that is different, and yet approximates the general shape of the appliance.

Specifically, the cross-linked polymers may be formed into a rectangular cross-sectional form 140 or alternatively, the form may be any shape, such as a dome or a flat sheet. This form is considered the initial or first state. Form 140 may be fabricated into an appliance 142 by thermoforming or similar process, with the desired surface features necessary for proper application of repositioning forces to the teeth. Appliance 142 is then allowed to cool below its glass transition temperature, while being restrained in the desired appliance shape. Appliance 142 will maintain this shape as long as the appliance is not exposed to temperatures above the pre-set glass transition temperature.

After being secured to the teeth and upon such time when removal is desired, the single-layered shell will be subjected to a thermal stimulus which causes the material to surpass its glass transition temperature. The change in temperature causes appliance 142 to return to its original state (e.g. form 140). Since the original state of form 140 has a different shape than appliance 142, the engagement forces are reduced.

Figure 6:
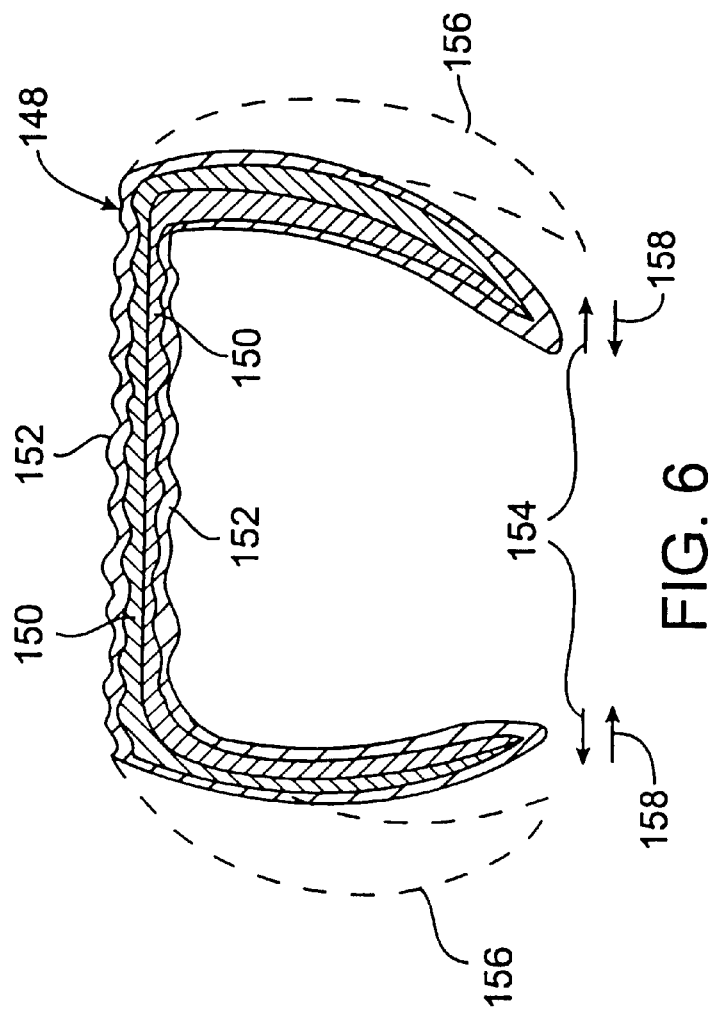
FIG. 6 is an illustration of a cross-sectional view of an embodiment of the present invention.

The memory removal mechanism can be made reversible. In an exemplary embodiment, form 140 may be made of a plurality of inner layers 150 sandwiched between an outer layer 152 as shown on appliance 148, illustrated in FIG. 6. The layers may have variable thickness and variable glass transition temperatures depending on the modulus requirements. The internal layers 150 may be made from a homopolymer, cross-linked homopolymer, copolymer, and/or cross-linked copolymer like those described in Examples 13–21. External layer 152 may be made of a Polycarbonate or similar material, which has a higher (or lower) glass transition temperature then the inner layers. The layers will be formed with the desired surface features and indentations necessary for proper application of the repositioning forces to the teeth.

In an exemplary operation of this embodiment, after the appliance has been applied to the teeth and upon such time as removal of the appliance is desired, a thermal stimulus is applied to shell 102. The temperature of the initiator is above the glass transition temperature of inner layers 150 but below the glass transition temperature of outer layer 152. Once inner layers 150 reach their glass transition temperature, they attempt to reconfigure to their original form, while outer layers 152 continue to maintain their original shape. The internal forces generated by the attempted reconfiguration of the inner layers, push outer layers 152 outward in the direction of arrows 154 until edges 116 and 1 18 reach positions 156. In moving the edges to positions 156, a reduction in the engagement forces between appliance 148 and the teeth is provided to allow for removal of the appliance.

The process may be reversed by cooling the shell below the glass transition temperature of the inner layers 150. Outer layers 152 maintain their useful shape and will continue to apply a biasing inward force in the direction of arrows 158 until the appliance returns to its original state.

In yet another embodiment of the glass transition removal mechanism, shown in FIGS. 3A and 3B, at least one anchor 124 may be used to secure the appliance to the teeth. In the same manner as the appliance, anchor 124 may be made of the same polymers described above, to undergo the same types of state changes. For example, anchor 124 may comprise a plurality of layers, but at least one layer, that include the formulations of materials in the above Examples. When subjected to a thermal stimulus, anchor 124 may undergo a glass transition. Accordingly, anchor 124 may either be configured to lose strength, change shape, or both, which will facilitate removal of the shell from the anchor.

All of the embodiments described above may be used either in combination or independently, subject to the discretion of the practitioner.

In each of the above described embodiments, the glass transition temperature is described as the threshold temperature for activating the state change process of the appliance. However, alternatively, the melting point temperature may be used as the threshold temperature. An advantage to using the melting point temperature is that the change in properties from one state to another is greater, Also, the change in property occurs over a smaller temperature range.

A variety of thermal stimuli have been identified which can be used to initiate the state changes in any of the embodiments described above. For example, the heat may be supplied to the appliance by introducing a source of heat energy, preferably a liquid because of its greater heat transfer capabilities. The heated liquid causes heat to rapidly transfer to the shell 102 to raise the temperature of the shell until the temperature reaches the transition temperature of the shell, causing the shell to transition to a second state.

Similarly magnetism, electricity, and radio waves can be used as secondary sources of heat to cause the desired state changes. Such external heat can also be applied by using an infrared, microwave, or radio frequency sources as well as resistive heating.

FORMULATIONS FOR ULTRA VIOLET AND/OR THERMALLY INTIATED POLYMERIZATION

| Material | Percent by Weight |
|---|---|
| Example 22. | |
| Methyl Methacrylate | 50% |
| Butyl Methacrylate | 15% |
| Hexyl Methacrylate | 30% |
| 1,4 Butanediol Dimethacrylate | 4.6% |
| USP 245 | .4% |
| Example 23. | |
| Isobutyl Methacrylate | 30% |
| Hexyl Methacrylate | 20% |
| Octadecyl Methacrylate | 22% |
| Polyethylene Glycol Dimethacrylate | 10% |

-continued

FORMULATIONS FOR ULTRA VIOLET AND/OR THERMALLY INTIATED POLYMERIZATION

| Material | Percent by Weight |
|---|---|
| Perkadox 16N | 0.3% |
| Methyl Methacylate | 18% |

Examples 22 and 23 are glass transition materials which may be polymerized either thermally using a conventional heat source or by using Ultra Violet (UV) light. If polymerization by U is desired then a UV initiator such as Duracure 1173 or benzoin methylether may be added in place of USP 245 or Perkadox 16N in Examples 22 and 23 above. The materials of Examples 22 and 23 may be used in the shell or in the anchor, as described above.

The removal mechanism of the present invention may also include polymers used together to provide a formulation which changes from a first state to a second state when subjected to an aqueous buffer solution having a predetermined pH ratio. Typical, material formulations as shown, for example, as Examples 24–27.

Typically, when the pH sensitive appliance is applied to the teeth, shell 102 will hydrate minimally, for example up to about 10%, when exposed to the pH level of the human mouth (normal physiological pH level). When the appliance is to be removed, the appliance may be subjected to a solution which will cause a change in the pH ratio of the mouth. Depending on the material formulation used, the change in pH causes the appliance to hydrate, for example, up to about 90% more than when at the normal pH level. When the appliance undergoes the change in hydrating states, the appliance changes dimension. For example, the linear dimension may change from about 2% to 300% when going from a lower hydration state to a higher hydration state. The swelling of the appliance removes its ability to properly engage the teeth.

FORMULATIONS FOR CHANGES BY ABSORPTION OF A LIQUID

| Material | Percent by Weight |
|---|---|
| Example 24. | |
| N-Vinyl Pyrrolidone | 25% |
| Butyl Acrylate | 40% |
| Isobornyl Methacrylate | 30% |
| 1, 6-Hexane Dioldimethacrylate | 5% |
| Azobis Isobutyl Nitrile | 0.5% |
| Example 25. | |
| 2-Hydroxy Ethylmethacrylate | 45% |
| Methyl Methacrylate | 35% |
| Butyl Methacrylate | 15% |
| Polyethylene Glycoldimethacrylate | 5% |
| Benzoyl Peroxide | 0.5% |
| Example 26. | |
| Methacrylic Acid | 20% |
| Methyl Methacrylate | 40% |
| Octadecyl Methacrylate | 35% |
| Ethylene Glycoldimethacrylate | 5% |
| Azobis Isobutyl Nitrile | 0.5% |
| Example 27. | |
| Acrylic Acid | 20% |
| Methyl Methacrylate | 40% |

-continued

FORMULATIONS FOR CHANGES BY ABSORPTION OF A LIQUID

| Material | Percent by Weight |
|---|---|
| Octadecyl Methacrylate | 35% |
| Ethylene Glycoldimethacrylate | 5% |
| Azobis Isobutyl Nitrile | 0.5% |

Alternatively, the anchor attachment may be made from the materials, such as those listed in Examples 24–27 and may be made to undergo a hydration state change when subjected to a different pH ratio. In one embodiment, while at the normal pH level, the attachment device may swell to a size that facilitates the engagement between the appliance and the teeth. For example, the hydration of the anchor may be up to about 90%. When the attachment device is exposed to a different pH level, the attachment device will dehydrate and shrink to disengage from the appliance. The range of dimensional change depends on the attachment device material composition, but will nonetheless be sufficient to allow for removal of the appliance. As before, the change in the appliance properties and in the attachment device may take place together or independently.

The removal mechanism may also respond to a state change caused by ionic strength changes, which causes water absorption in polymers subjected to different concentration of salts, including NaCl or sugar.

Typically, when the appliance is applied to the teeth, the shell will hydrate minimally, for example up to about 10%, based on the average concentration of salts in the human mouth (normal ionic strength). When the appliance is to be removed, the appliance may be subjected to a solution which will cause a change in the concentration of the salts. Depending on the material formulation used, the change in salt concentration causes the appliance to hydrate, for example, up to about 90% more than when in the normal concentration ranges. Exemplary material formulations are described in Examples 28 and 29. When the appliance undergoes the change in hydrating states, the appliance changes dimension. For example, the linear dimension may change from about 2% to 300% when going from a lower hydration state to a higher hydration state.

FORMULATION FOR CHANGES BY ABSORPTION OF A LIQUID IN DIFFERENT IONIC STRENGTH CONDITIONS

| Material | Percent by Weight |
|---|---|
| Example 28. | |
| N-Vinyl Pyrrolidone | 25% |
| Butyl Acrylate | 40% |
| Isobornyl Methacrylate | 30% |
| 1, 6-Hexane Dioldimethacrylate | 5% |
| Azobis Isobutyl Nitrile | 0.5% |
| Example 29. | |
| 2-Hydroxy Ethylmethacrylate | 45% |
| Methyl Methacrylate | 35% |
| Butyl Methacrylate | 15% |
| Polyethylene Glycoldimethacrylate | 5% |
| Benzoyl Peroxide | 0.5% |

Alternatively, the anchor attachment may also be made from materials in Examples 28 and 29 and may undergo a hydration state change when subjected to a different concentration of salts. While in its initial state, the attachment device may swell to a size that facilitates the engagement between the appliance and the teeth. For example, the hydration of the anchor may be up to about 90%. When the attachment device is exposed to a different concentration of salts, the attachment device will dehydrate and shrink to disengage from the appliance. The range of dimensional change depends on the attachment device material composition. As before, the change in the appliance properties and in the attachment device may take place together or independently.

While the above is a complete description of the preferred embodiments of the invention, various alternatives, modifications, and equivalents may be used. In one example, appliance 100 may be removed from the teeth when a pressure is directed down on the top surface of the teeth, either through biting down or through a direct manual application of the pressure. The pressure may force edges 116 and 118 in an outward direction, thus removing engagement between the appliance and interfaces on the teeth.

Therefore, the above description should not be taken as limiting the scope of the invention which is defined by the appended claims.

What is claimed is:

1. A system of dental positioning adjustment appliances comprising:
   a plurality of incremental position adjustment appliances, each of said appliances comprising:
   a shell including at least one layer of a polymeric material and having a cavity which fits closely over a contiguous group of teeth, the at least one layer of polymeric material having a first state where the appliance is held onto the teeth and a second state where the appliance may be removed from the teeth.

2. A system as in claim 1, wherein the polymeric material exists in the second state when exposed to a non-oral environment.

3. A system as in claim 2, wherein the non-oral environment is selected from the group consisting of non-physiologic temperature, non-physiologic pH, and non-physiologic ionic strength.

4. A system as in claim 1, wherein the polymeric material is converted to the second state by exposure to energy selected from the group consisting of mechanical energy and electromagnetic energy.

5. A system as in claim 1, wherein the shell has cavities shaped to receive and resiliently reposition teeth from one arrangement to a successive arrangement.

6. A system as in claim 1, wherein the at least one layer comprises a material selected from the group consisting of memory polymers, methacrylate containing polymers, acrylate containing polymers, thermoplastic polymers, cross-linked thermoplastic polymers, thermoplastic polymer blends, cross-linked thermoplastic polymer blends, thermoplastic elastomer polymers, and thermoset polymers.

7. A system for repositioning teeth comprising:
   a plurality of incremental position adjustment appliances, each of said appliances comprising:
   a polymeric shell having cavities shaped to receive and resiliently reposition teeth from one arrangement to a successive arrangement; and
   a removal mechanism coupled to each of the polymeric shells, the removal mechanism being switchable from a first state where the shell is held onto the teeth to a second state where the shell may be removed from the teeth.

8. A system as in claim 7, wherein the removal mechanism comprises at least one polymeric layer laminated to at least a portion of the polymeric shell.

9. A system. as in claim 8, wherein the polymeric layer comprises a material selected from the group consisting of memory polymers, methacrylate containing polymers, acrylate containing polymers, thermoplastic polymers, cross-linked thermoplastic polymers, thermoplastic polymer blends, cross-linked thermoplastic polymer blends, thermoplastic elastomer polymers, and thermoset polymers.

10. A system as in claim 7, wherein the removal mechanism comprises a plurality of polymeric layers laminated to the shell, wherein at least one of the plurality of layers undergoes the state switch.

11. A system as in claim 7, wherein the removal mechanism comprises a plurality of polymeric layers laminated to the shell, wherein each layer undergoes the state switch independent of the other layers.

12. A system as in claim 7, wherein the removal mechanism comprises an adhesive within at least a portion of the cavities, the adhesive having a first peel strength when in the first state and a second peel strength when in the second state.

13. A system as in claim 7, wherein the removal mechanism is formed at least in part from a material having a first state with a first modulus and a second state with a second modulus, the first modulus being different from the second modulus.

14. A system as in claim 7, wherein the removal mechanism is a structure, the structure having a first state with a first deformation and a second state with a second deformation, the first deformation being different from the second deformation.

15. A system as in claim 7, wherein the removal mechanism switches from the first state to the second state in response to an environmental stimulus.

16. A system as in claim 15, wherein the environmental stimulus is selected from the group consisting of temperature, ionic strength, pH ratio, and liquid absorption.

17. A system as in claim 7, wherein the removal mechanism switches from the first state to the second state in response to an external stimulus.

18. A system as in claim 17, wherein the external stimulus is selected from the group consisting of light, magnetism, electricity, and radio waves.

19. A system as in claim 1, wherein at least a portion of the shell has a stiffness in the range from 0.1 GPa to 4 GPa in the first state and wherein the stiffness is reduced by at least 10% in the second state.

20. A system as in claim 19, wherein at least a portion of the shell has a stiffness in the range from 0.1 GPa to 4 GPa in the first state and wherein the stiffness is reduced by at least 90% in the second state.

21. A system for repositioning teeth comprising:
   a plurality of incremental position adjustment appliances, each of said appliances comprising;
   a polymeric shell having a cavity shaped to receive and resiliently reposition teeth from one arrangement to a successive arrangement; and
   an attachment device which couples to the shell of each shell, the attachment device having a first state where the shell is held onto the teeth and a second state where the shell may be removed from the teeth.

22. A system as in claim 21, wherein the attachment device is positionable between an outer surface of the teeth and an inner surface of the cavity.

23. A system as in claim 21, wherein the attachment device is an anchor device.

24. A system as in claim 23, wherein the anchor comprises a geometric shape, the geometric shape allowing installation of the shell on to the teeth and restricting removal of the shell when the anchor device is in the first state.

25. A system as in claim 21 wherein the attachment device comprises at least one polymeric layer laminated to at least a portion of the attachment device.

26. A system as in claim 25, wherein the polymeric layer comprises a material selected from the group consisting of memory polymers, methacrylate containing polymers, acrylate containing polymers, thermoplastic polymers, cross-linked thermoplastic polymers, thermoplastic polymer blends, cross-linked thermoplastic polymer blends, thermoplastic elastomer polymers, and thermoset polymers.

27. A system as in claim 21, wherein the attachment device comprises a plurality of polymeric layers laminated to the attachment device, wherein at least one of the plurality of layers undergoes the state switch.

28. A system as in claim 21, wherein the attachment device comprises a plurality of polymeric layers laminated to the attachment device, wherein each layer undergoes the state switch independent of the other layers.

29. A system as in claim 21, wherein the attachment device switches from the first state to the second state in response to an environmental stimulus.

30. A system as in claim 29, wherein the environmental stimulus is selected from the group consisting of temperature, ionic strength, pH ratio, and liquid absorption.

31. A system as in claim 21, wherein the attachment device switches from the first state to the second state in response to an external stimulus.

32. A system as in claim 31, wherein the external stimulus is selected from the group consisting of light, magnetism, electricity, and radio waves.

33. A system as in claim 21, wherein the attachment device is embedded within the shell.

34. A system as in claim 33, wherein the attachment device is a structure selected from the group consisting of wires, filaments, meshes, rings, and braids.

35. A system as in claim 33, wherein at least a portion of the attachment device comprises a shape memory alloy, the alloy being reconfigured when subjected to an external stimulus.

36. A system comprising:
a plurality of incremental position adjustment appliances, each of said appliances comprising;
  a shell including at least one layer of a polymeric material and having a cavity which fits closely over a contiguous group of teeth; and
  an attachment device coupled to each shell and positionable between an outer surface of the teeth and an inner surface of the cavity,
  the at least one layer of polymeric material and the attachment device each having a first state where the shell is held onto the teeth and a second state where the shell may be removed from the teeth.

* * * * *